US012721950B2

(12) United States Patent
Yin

(10) Patent No.: US 12,721,950 B2
(45) Date of Patent: Sep. 1, 2026

(54) MEDICAMENT DELIVERY MEMBER MODULES

(71) Applicant: SHL Medical AG, Zug (CH)

(72) Inventor: Ming-Ting Yin, Taoyuan City (TW)

(73) Assignee: SHL Medical AG, Zug (CH)

( * ) Notice: Subject to any disclaimer, the term of this patent is extended or adjusted under 35 U.S.C. 154(b) by 428 days.

(21) Appl. No.: 18/553,644

(22) PCT Filed: Mar. 22, 2022

(86) PCT No.: PCT/EP2022/057526
§ 371 (c)(1),
(2) Date: Oct. 2, 2023

(87) PCT Pub. No.: WO2022/248098
PCT Pub. Date: Dec. 1, 2022

(65) Prior Publication Data

US 2024/0181170 A1 Jun. 6, 2024

Related U.S. Application Data

(60) Provisional application No. 63/193,133, filed on May 26, 2021.

(51) Int. Cl.
*A61M 5/32* (2006.01)

(52) U.S. Cl.
CPC ........ *A61M 5/3202* (2013.01); *A61M 5/3245* (2013.01); *A61M 2005/3254* (2013.01)

(58) Field of Classification Search
CPC .. A61M 2005/2474; A61M 2005/3254; A61M 5/3202; A61M 5/3245;
(Continued)

(56) References Cited

U.S. PATENT DOCUMENTS 8,932,254 B2 1/2015 Eaton
9,757,521 B2 9/2017 McLoughlin et al.
(Continued)

FOREIGN PATENT DOCUMENTS

CN 102971024 A 3/2013
CN 112512611 A 3/2021
(Continued)

OTHER PUBLICATIONS

International Search Report received for International Application No. PCT/EP2022/057526, mailed on Jul. 27, 2022, 3 pages.
(Continued)

*Primary Examiner* — Thomas P Burke
(74) *Attorney, Agent, or Firm* — ALSTON & BIRD LLP

(57) ABSTRACT

A medicament delivery member module (to) for a medicament delivery device is disclosed, the medicament delivery member module (to) comprising a proximal shield (30), a distal shield (50) and a medicament delivery member hub (70), and the medicament delivery member module (10) extending along a longitudinal axis (12) in an axial direction (13) from a proximal end (14) to a distal end (15). The proximal shield (30) comprises a first surface (31) facing towards the longitudinal axis (12) and a second surface (32) facing away from the longitudinal axis (12). The medicament delivery member hub (70) comprises a third surface (73) facing away from the longitudinal axis (12) and the distal shield (50) comprises a fourth surface (54) facing towards the longitudinal axis. The proximal shield (30) is moveable in the axial direction (13) relative to the distal shield (50) from a proximal position to a distal position.

15 Claims, 4 Drawing Sheets

(58) Field of Classification Search
CPC ................ A61M 5/322; A61M 5/3257; A61M 2005/3258; A61M 5/326; A61M 2005/3267
See application file for complete search history.

(56) References Cited

U.S. PATENT DOCUMENTS

| | | | | |
|---|---|---|---|---|
| 10,300,213 | B2 | 5/2019 | Bengtsson et al. | |
| 10,561,793 | B2 | 2/2020 | Finke et al. | |
| 10,874,800 | B2 | 12/2020 | Schader et al. | |
| 11,007,327 | B2 | 5/2021 | Bengtsson et al. | |
| 2003/0120209 | A1* | 6/2003 | Jensen | G09F 1/04 604/110 |
| 2007/0021718 | A1 | 1/2007 | Burren et al. | |
| 2008/0177237 | A1* | 7/2008 | Stonehouse | A61M 5/326 604/263 |
| 2010/0042047 | A1* | 2/2010 | Suzuki | A61M 5/326 604/110 |
| 2013/0237905 | A1* | 9/2013 | Holmqvist | A61M 5/19 604/89 |
| 2014/0163518 | A1* | 6/2014 | Epstein | A61M 5/3234 604/110 |
| 2015/0157807 | A1* | 6/2015 | Srinivasan | A61M 5/3257 604/198 |
| 2015/0273161 | A1 | 10/2015 | Bengtsson et al. | |
| 2015/0320939 | A1* | 11/2015 | Beek | A61M 5/326 604/193 |
| 2018/0161504 | A1 | 6/2018 | Kemp et al. | |
| 2018/0169338 | A1 | 6/2018 | Mosebach et al. | |
| 2018/0353709 | A1 | 12/2018 | Schader et al. | |
| 2020/0129699 | A1 | 4/2020 | Helmer | |
| 2020/0188605 | A1 | 6/2020 | Boström | |
| 2020/0282151 | A1 | 9/2020 | Liscio | |
| 2020/0338277 | A1 | 10/2020 | Franke et al. | |
| 2020/0360621 | A1 | 11/2020 | Franke et al. | |
| 2020/0376200 | A1 | 12/2020 | Zucker et al. | |
| 2021/0178082 | A1* | 6/2021 | Franke | A61M 5/31501 |
| 2022/0023549 | A1* | 1/2022 | Whyte | A61M 5/3257 |
| 2022/0111155 | A1* | 4/2022 | Py | A61M 5/3221 |
| 2023/0355892 | A1* | 11/2023 | Calderwood | A61M 5/3243 |

FOREIGN PATENT DOCUMENTS

| | | | |
|---|---|---|---|
| EP | 2021054 | B1 | 3/2010 |
| EP | 2346552 | B1 | 8/2012 |
| EP | 2875838 | A1 | 5/2015 |
| EP | 2892590 | B1 | 1/2018 |
| EP | 3302630 | A1 | 4/2018 |
| EP | 3302635 | A1 | 4/2018 |
| EP | 3360591 | A1 | 8/2018 |
| EP | 3380134 | A1 | 10/2018 |
| EP | 3492126 | A1 | 6/2019 |
| EP | 3569271 | A1 | 11/2019 |
| EP | 3727502 | A1 | 10/2020 |
| EP | 3727516 | A1 | 10/2020 |
| EP | 3823701 | A1 | 5/2021 |
| GB | 2467904 | A | 8/2010 |
| WO | WO 2009/094793 | A1 | 8/2009 |
| WO | WO 2015/185664 | A1 | 12/2015 |
| WO | WO 2020/070327 | A1 | 4/2020 |
| WO | WO 2020/104812 | A1 | 5/2020 |
| WO | WO 2020/169842 | A1 | 8/2020 |
| WO | WO 2022/128520 | A1 | 6/2022 |

OTHER PUBLICATIONS

Written Opinion of the International Searching Authority received for International Application No. PCT/EP2022/057526, mailed on Jul. 7, 2022, 4 pages.

Chinese Application No. 202280036138, First Office Action mailed Apr. 9, 2026.

* cited by examiner 17
12
10
16
14
72
30
13
70
50
15
90

30
34
38
32
36
31
36
50

54
58
55
59
56
70
72
78
73
71
74
76
79

30
72
36
31
32
70
73
58
74
50
54
76

31
32
54
73
74
76
55
34

54
73
31
32

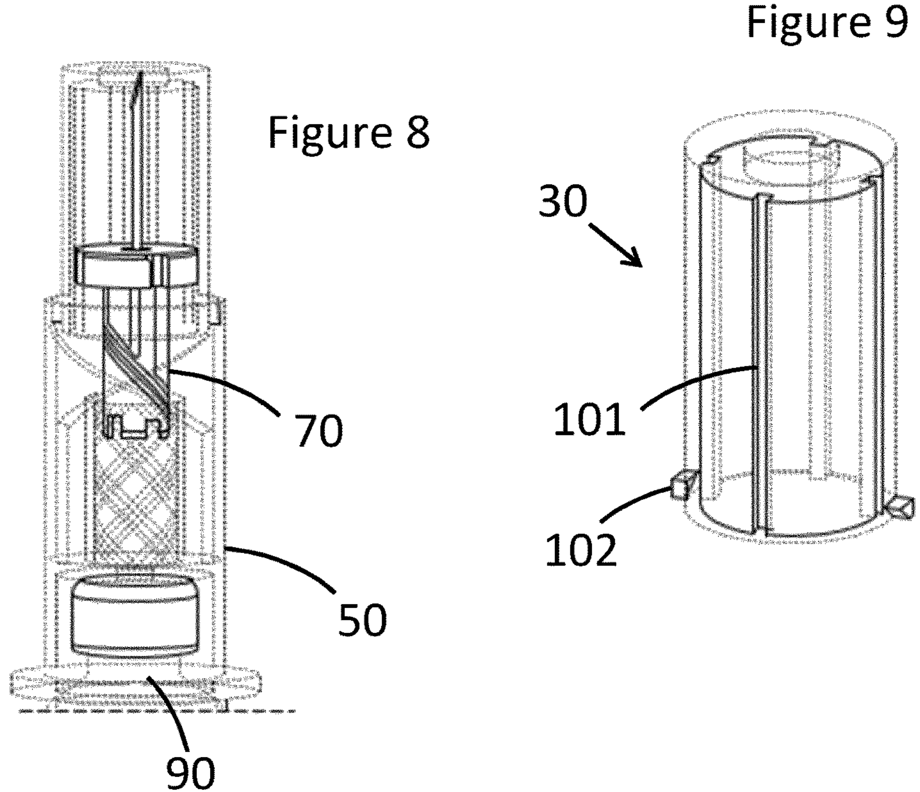
Figure 8
70
50
90
Figure 9
30
101
102
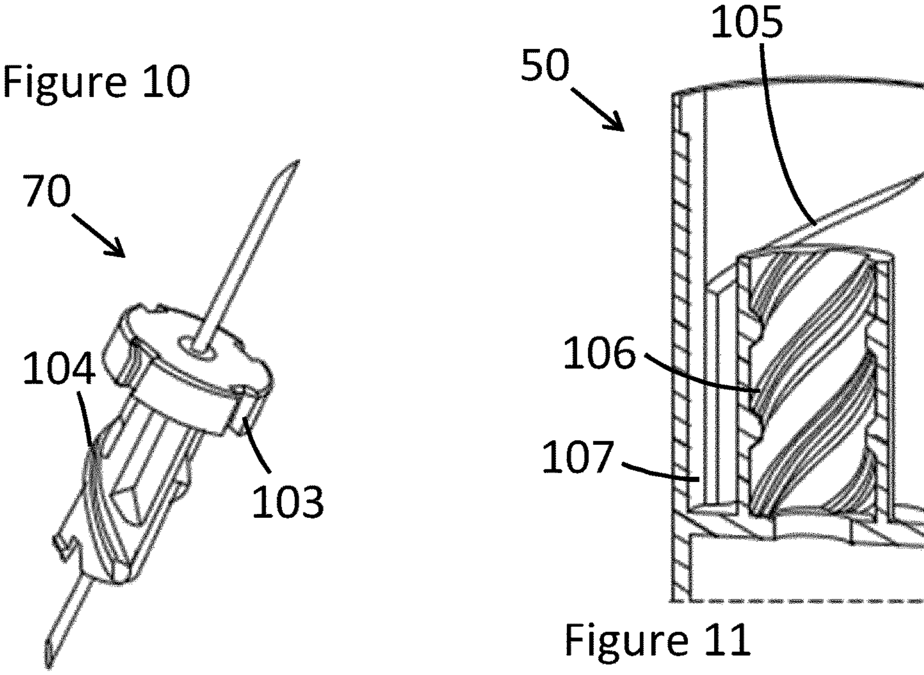
Figure 10
70
104
103
105
50
106
107
Figure 11

MEDICAMENT DELIVERY MEMBER MODULES

CROSS REFERENCE TO RELATED APPLICATIONS

This application is a National Stage Application, filed under 35 U.S.C. § 371, of International Application No. PCT/EP2022/057526, filed Mar. 22, 2022, which claims priority to U.S. Provisional Patent Application No. 63/193,133, filed May 26, 2021; the contents of both of which are hereby incorporated by reference in their entirety.

TECHNICAL FIELD

Medicament delivery member modules for medicament delivery devices.

BACKGROUND

In cartridge-based medicament delivery devices such as autoinjectors, it is important that the medicament delivery member (e.g. a needle) is kept safe before use, both to avoid needle stick injuries and also to maintain sterility. In addition, cartridge-based medicament delivery devices are typically provided with the medicament delivery member separated from the medicament container, which means that the user typically has to somehow attach the medicament delivery member to the medicament container before carrying out an injection.

This adds extra steps and therefore extra complexity to device usage, which is undesirable in terms of ease of use. Considering this, the applicant has appreciated that improvements can be made in comparison to existing designs.

SUMMARY

Reference should now be made to the appended claims.

An aspect concerns a medicament delivery member module for a medicament delivery device, the medicament delivery member module comprising a proximal shield, a distal shield and a medicament delivery member hub, the medicament delivery member module extending along a longitudinal axis in an axial direction from a proximal end to a distal end, wherein the proximal shield comprises a first surface facing towards the longitudinal axis and a second surface facing away from the longitudinal axis, wherein the medicament delivery member hub comprises a third surface facing away from the longitudinal axis and the distal shield comprises a fourth surface facing towards the longitudinal axis, wherein the proximal shield is moveable in the axial direction relative to the distal shield from a proximal position to a distal position, wherein the medicament delivery member module is arranged so that in a first part of a movement of the proximal shield from the proximal position to the distal position, the first surface and the third surface are in contact with one another and the second surface and the fourth surface are in contact with one another, and the friction between the first surface and the third surface is greater than the friction between the second surface and the fourth surface, so that during the first part of the movement of the proximal shield from the proximal position to the distal position, the medicament delivery member hub moves with the proximal shield, wherein the medicament delivery member module is arranged so that in a subsequent part (which is after the first part) of the movement of the proximal shield from the proximal position to the distal position, the first surface and the third surface are in contact with one another and the second surface and the fourth surface are spaced apart from one another (typically in the axial direction), and the medicament delivery member hub is restricted from further movement in the distal direction, so that the proximal shield moves in the distal direction relative to both the distal shield and the medicament delivery member hub during the subsequent part of the movement of the proximal shield from the proximal position to the distal position. When used, this can allow the medicament delivery member to puncture a cartridge first and then subsequently puncture an injection site.

Optionally, the first surface and the second surface are both on a protrusion. Optionally, the protrusion is compressible. Optionally, the protrusion is on a tab of the proximal shield. Optionally, the tab is at a distal end of the proximal shield. Optionally, the third surface comprises a protrusion. This can increase the friction between the first surface and the third surface. Optionally, the protrusion is a rib that extends circumferentially around the longitudinal axis. Optionally, the third surface comprises a plurality of protrusions that are spaced apart from one another in the axial direction. Optionally, the plurality of protrusions are ribs that extend circumferentially around the longitudinal axis.

Optionally, the proximal shield is at least partially inside the distal shield. Optionally, the medicament delivery member hub is at least partially inside the proximal shield. Optionally, the proximal shield, the distal shield and the medicament delivery member hub are coaxial. Optionally, the proximal shield is arranged telescopically inside the distal shield.

Optionally, one or more of the proximal shield and the distal shield comprises a seal that is pierced by the medicament delivery member during movement of the proximal shield relative to the distal shield.

Optionally, the proximal shield is tubular. Optionally, the proximal shield is cylindrical. Optionally, the distal shield is tubular. Optionally, the distal shield is cylindrical. Optionally, the needle hub is cylindrical. Optionally, the proximal shield is closer to the proximal end of the needle module than the distal shield.

Optionally, the needle hub comprises a medicament delivery member. Optionally, the medicament delivery member is a needle.

Optionally, the proximal shield is moveable in the axial direction relative to the distal shield from an initial position to the proximal position, wherein in the initial position, the first surface and the third surface are in contact with one another and the second surface and the fourth surface are spaced apart from one another, and wherein the medicament delivery member module is arranged so that the proximal shield and the medicament delivery member hub move in the distal direction relative to the distal shield when the medicament delivery member module moves from the initial position to the proximal position.

Optionally, the distal shield comprises a fifth surface, wherein the fifth surface faces in the proximal direction, and wherein the medicament delivery member hub comprises a sixth surface, wherein the sixth surface faces in the distal direction, and wherein the fifth surface is arranged to be in contact with the sixth surface during the subsequent part of the movement stroke so that the medicament delivery member hub is restricted from further movement in the distal direction during the subsequent part of the movement stroke.

An aspect concerns a sub-assembly of a medicament delivery device comprising a cartridge and any medicament delivery member module as described above. Optionally, the cartridge comprises a fifth surface, wherein the fifth surface faces in the proximal direction, and wherein the medicament delivery member hub comprises a sixth surface, wherein the sixth surface faces in the distal direction, and wherein the fifth surface is arranged to be in contact with the sixth surface during the subsequent part of the movement stroke so that the medicament delivery member hub is restricted from further movement in the distal direction during the subsequent part of the movement stroke.

An aspect concerns a cartridge assembly for attaching to a powerpack of a medicament delivery device, the cartridge assembly comprising any medicament delivery member module described above or any sub-assembly described above.

An aspect concerns a medicament delivery device comprising any medicament delivery member module described above, any sub-assembly described above, or any cartridge assembly described above. Optionally, the medicament delivery device is an autoinjector.

An aspect concerns a method of actuating a needle module of a medicament delivery device so that a distal end of a needle pierces a cartridge and a proximal end of the needle pierces an injection site, the method comprising the following steps in the following order: pushing a proximal shield and a needle hub comprising the needle in a distal direction relative to a distal shield, the proximal shield and the needle hub being held together by friction between the proximal shield and the needle hub; and pushing the proximal shield in the distal direction relative to the distal shield and the needle hub, with the friction between the proximal shield and the needle hub being overcome by engagement of the needle hub with the distal shield or by engagement of the needle hub with another medicament delivery device component.

BRIEF DESCRIPTION OF THE DRAWINGS

Embodiments of the present disclosure will now be described by way of example only and with reference to the following accompanying drawings.

FIGS. 8 to 13 show another needle module.

DETAILED DESCRIPTION

As a built-in needle module for a cartridge-based drug cassette, the concept described herein elaborates on how to switch a needle cover compression stroke into two different sub-steps in sequence: attaching a needle to a cartridge then subsequently having the needle penetrate an injection site.

In general, the needle cover can be used to trigger the device and sequentially control the needle piercing the cartridge septum and the injection site. The sequential control is provided by the arrangement of tabs of the front shield (proximal shield), the embossed feature of the needle hub and inwardly protruding ribs of the rear shield (distal shield). A possible advantage of this is that only the front shield, rear shield and needle hub need a sterilisation step.

Figures 1, 2, 3, 4:
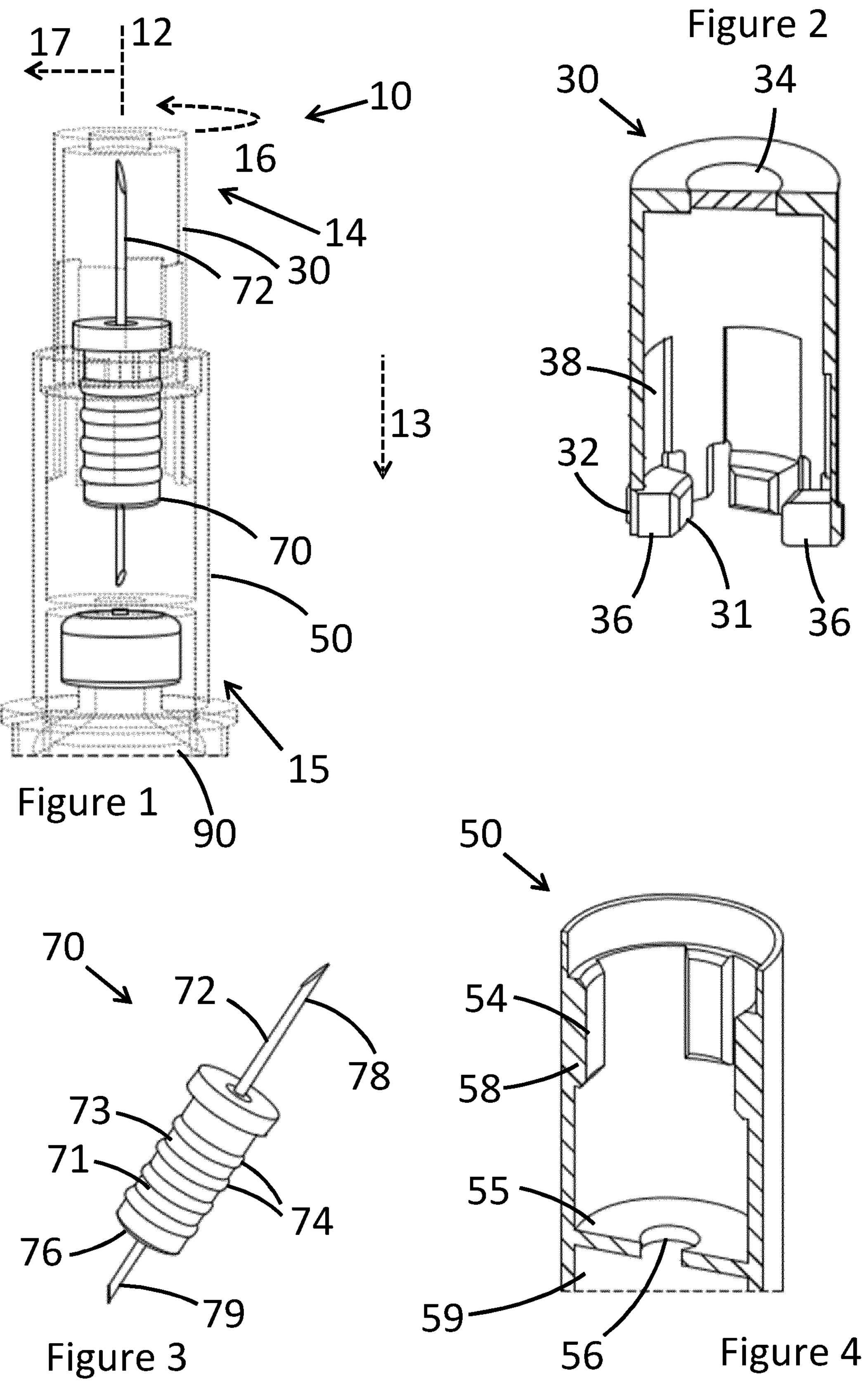
FIG. 1 shows a perspective view of a needle module, with parts of the module shown as see-through (dotted lines).
FIG. 2 shows a perspective cross-section view of the proximal shield of FIG. 1.
FIG. 3 shows a perspective view of the needle hub of FIG. 1.
FIG. 4 shows a perspective cross-section view of part of the distal shield of FIG. 1.

A first example of a medicament delivery member module is a needle module 10 as shown in FIG. 1. The needle module 10 comprises a proximal shield (or front shield or first shield) 30, a distal shield (or rear shield or second shield) 50 and a needle hub 70. The needle hub 70 comprises a needle 72. Part of a cartridge 90 is also shown for reference. The needle hub 70 extends along a longitudinal axis 12 in an axial direction 13 from a proximal end 14 to a distal end 15. For context, a circumferential direction 16 relative to the axis 12 and a radial direction 17 relative to the axis 12 are also shown.

As shown in FIG. 2, the proximal shield 30 comprises a first surface 31 facing towards the axis and a second surface 32 facing away from the axis. As shown in FIG. 3, the needle hub 70 comprises a third surface 73 facing away from the axis. As shown in FIG. 4, the distal shield 50 comprises a fourth surface 54 facing towards the axis.

The proximal shield 30 is moveable in the axial direction 13 relative to the distal shield 50 from a proximal position to a distal position, as described in more detail below with reference to FIGS. 5 to 7.

The needle module is arranged so that in a first part of a movement of the proximal shield from the proximal position to the distal position, the first surface 31 and the third surface 73 are in contact with one another and the second surface 32 and the fourth surface 54 are in contact with one another, and the friction between the first surface 31 and the third surface 73 is greater than the friction between the second surface 32 and the fourth surface 54. The result of this is that during the first part of the movement from the proximal position to the distal position, the needle hub 70 moves with the proximal shield 30.

The needle module is also arranged so that in a subsequent part of the movement of the proximal shield from the first position to the second position, the first surface 31 and the third surface 73 are in contact with one another and the second surface 32 and the fourth surface 54 are spaced apart from one another in the axial direction 13, and the needle hub 70 is restricted from further movement in the distal direction. The result of this is that the proximal shield 30 moves in the distal direction relative to both the distal shield 50 and the needle hub 70 during the subsequent part of the movement from the proximal position to the distal position.

The structure of the proximal shield 30, the distal shield 50 and the needle hub 70 will now be described in more detail with reference to FIGS. 2 to 4. FIG. 2 shows the proximal shield 30. In particular, the proximal shield 30 comprises a first surface 31 that faces towards the axis 12 and a second surface 32 that faces away from the axis 12. The proximal shield is tubular (and more specifically is cylindrical), with a closed proximal end and an open distal end. The proximal end comprises an optional seal 34; this seal can be pierced by the needle 72. Alternatively, a hole in the proximal end could be provided in the location of the seal 34, in a similar manner to a hole 56 of the distal shield (see FIG. 4), though provision of a seal can help with sterility.

At the distal end of the proximal shield, a plurality of tabs 36 (four in this case, although one, two, or more could be provided) are spaced out in the circumferential direction around the open distal end. Each tab 36 comprises a protrusion comprising a first surface 31 and a second surface 32. Each tab is at least partly made of a compressible material such as rubber or a thermoplastic elastomer (TPE). In this example, the first surface 31 is further away from the axis than the outer surface of the rest of the proximal shield 30, due to the protrusion. In this example, the second surface 32 is closer to the axis than the inner surface of the rest of the proximal shield 30 (so closer to the surface than the cylindrical part of the proximal shield 30), due to the protrusion. Optional recesses 38 are also provided in the inner surface of the proximal shield adjacent to the tabs 36; these recesses can help allow the tabs to flex. Allowing the tabs to flex is optional, but can help the proximal shield 30 to slide past the needle hub 70 in the subsequent part of the movement of the proximal shield from the first position to the second position. Alternatively, the tabs could be flexible arms.

FIG. 3 shows the needle hub 70. In particular, the needle hub 70 comprises a third surface 73 that faces away from the axis. The third surface comprises a plurality of protrusions 74. The needle hub 70 comprises a base 71 and a needle 72. The needle 72 comprise a proximal part 78 and a distal part 79. The proximal part 78 is designed to pierce an injection site to deliver a medicament. The distal part is designed to pierce a cartridge to access a medicament in the cartridge.

FIG. 4 shows the distal shield 50. In particular, the distal shield 50 comprises a fourth surface 54 that faces towards the axis. The distal shield is tubular (and more specifically is cylindrical), with a partially closed distal end and an open proximal end. A wall comprising a fifth surface 55 partially closes the distal end, apart from a hole 56. The hole can optionally be closed with a seal; the seal would be pierced by the distal end of the needle during use. A plurality of protrusions 58 (four in this case, although one, two, or more could be provided, depending for example on the number of tabs 36) is provided, with each protrusion 58 comprising a fourth surface 54.

The distal shield 50 also comprises a recess 59 at the distal end of the distal shield 50. The recess is formed by part of the cylindrical walls of the distal shield 50 and by the wall that comprises the fifth surface 55. The recess is optional, but can be beneficial as it can guide placement of a cartridge and/or support the cartridge during medicament delivery device assembly, and/or support the cartridge in a completed medicament delivery device.

The relative movement of the components of the needle module 10 during use of a medicament delivery device comprising the module will now be described using FIGS. 5 to 7. The proximal shield is moveable from an optional initial position (FIG. 5) to a proximal position to a distal position to a final position. FIG. 6 shows a position between the proximal position and the distal position, and FIG. 7 shows a position between the distal position and the final position.

Figures 5, 6, 7:
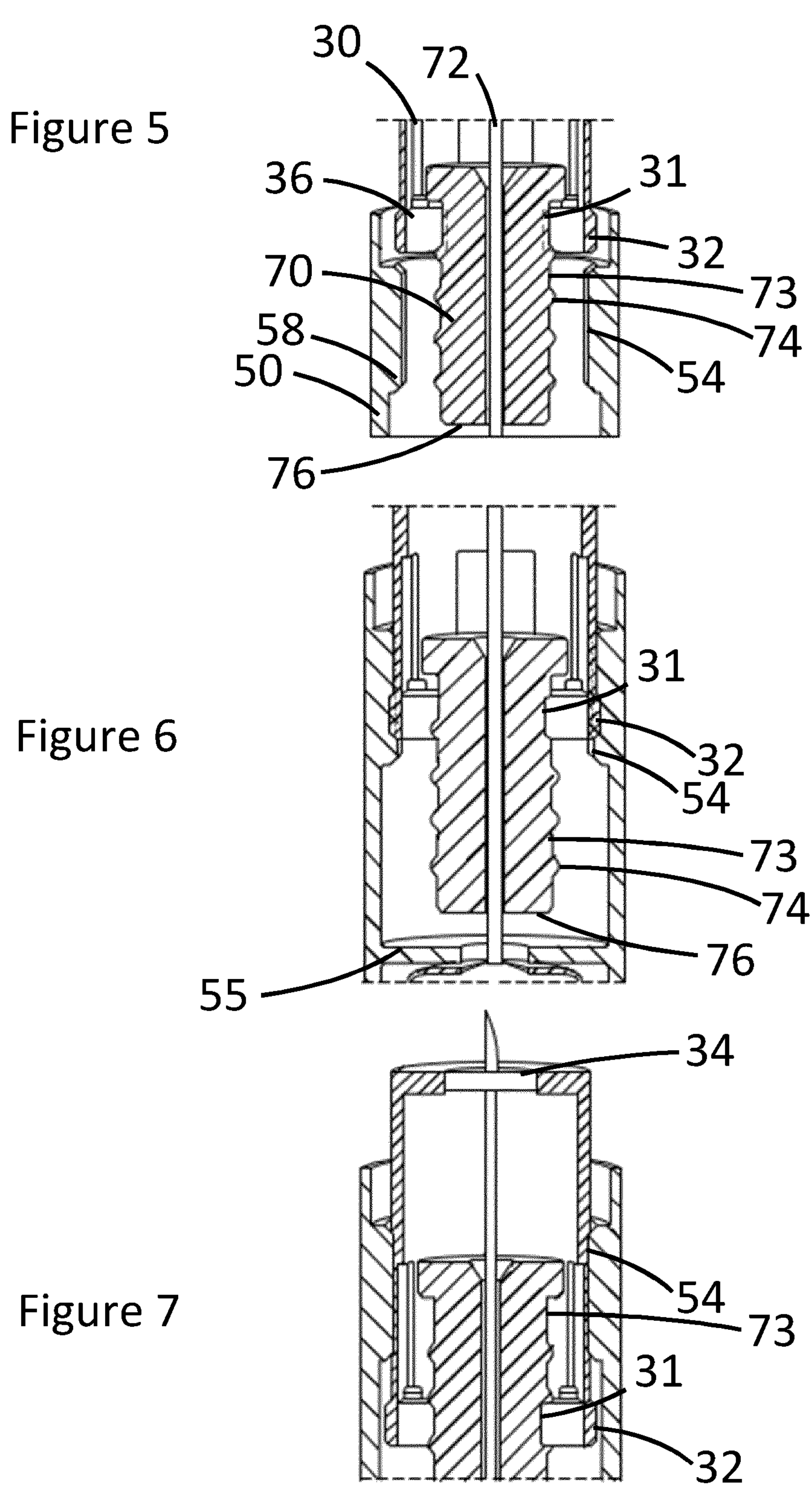
FIGS. 5 to 7 show cross-section views of the needle module of FIG. 1 before and during use.

An optional initial position is shown in FIG. 5, in which the first surface 31 and the third surface 73 are in contact with one another, the second surface 32 and the fourth surface 54 are spaced apart from one another, and the fifth surface 55 and the sixth surface 76 are spaced apart from one another. In this position, the compressible material of the tab is not compressed (or is partially compressed) between the third surface 73 and the fourth surface 54, which can increase shelf life by providing the stored product in an uncompressed (or less compressed) state. This initial position is optional, and the needle module 10 could be provided directly in the proximal position, particularly in examples that do not use a compressible material (as described below).

When a medicament delivery device is prepared for use, various steps may be taken, including rotation of a part, removal of a cap and/or another part, and/or pressing a button. It is envisioned that the ideas described herein could be particularly useful in devices in which a needle guard is provided which is pushed in the distal direction relative to the housing of the device to expose the needle so that the needle can penetrate the injection site and to also activate medicament delivery. The needle guard moving in the distal direction can then provide the force required to push the proximal shield in the distal direction relative to the distal shield (with movement of the distal shield being axially restricted relative to the housing of the device), though the force could alternatively be provided in another way, for example by the user prior to use of the device.

When the proximal shield is pushed in the distal direction relative to the distal shield, the proximal shield will move in the distal direction along with the needle hub, as friction between the first surface 31 and the third surface 73 makes the needle hub 70 and the proximal shield 30 move together. This movement results in the second surface 32 and the fourth surface 54 coming into contact. This point is the proximal position, which could also be the position in a completed medicament delivery device as described above, as the initial position is optional. As the friction between the first surface 31 and the third surface 73 is greater than the friction between the second surface 32 and the fourth surface 54, the needle hub 70 and the proximal shield 30 will (continue to) move together in the distal direction relative to the distal shield 50, thereby reaching the position shown in FIG. 6.

As the needle hub 70 and the proximal shield 30 continue to move together in the distal direction relative to the distal shield 50, the proximal shield reaches a point at which the second surface 32 and the fourth surface 54 are no longer in contact (i.e. spaced apart). The needle hub 70 and the proximal shield 30 still continue to move together in the distal direction relative to the distal shield 50 due to the contact and resulting friction between the first surface 31 and the third surface 73.

Next, the fifth surface 55 and the sixth surface 76 contact each other, providing a greater resistance to the continued distal movement of the needle hub relative to the distal shield than the friction between the first surface 31 and the third surface 73. By the time the fifth surface 55 and the sixth surface 76 contact each other, the needle 72 has pierced the cartridge.

Optionally, the fifth surface 55 and the sixth surface 76 contact each other while the second surface 32 and the fourth surface 54 are still in contact, though this may increase the resistance of the proximal shield moving in the distal direction relative to the distal shield, which in some cases may be disadvantageous.

Due to the resistance provided by the fifth surface 55 and the sixth surface 76 being in contact, the continued movement of the proximal shield 30 in the distal direction relative to the distal shield 50 results in the movement of the proximal shield 30 in the distal direction relative to both the distal shield 50 and the needle hub 70. This results in the needle 72 piercing the seal 34, as shown in FIG. 7.

In the final position, the needle extends out of the proximal end of the proximal shield and the needle extends out of the distal end of the distal shield. As a result, the needle is able to pierce an injection site at the proximal end of the needle and is able to pierce a cartridge at the distal end of the needle. In the final position, the proximal shield 30 is in its distal-most position relative to the distal shield 50, and the needle hub is also in its distal-most position relative to the distal shield 50. The needle module is also typically at its shortest length in the axial direction (and the needle module is typically at its longest length in the axial direction in the assembled medicament delivery device).

It is envisioned that the needle modules described herein would primarily be used with medicament delivery devices with needleless containers such as cartridges. These devices could be single use or multi-use. The medicament delivery device could be provided as a single cohesive unit that cannot be disassembled by a user, or could be two or more parts that a user has to assemble together before using the medicament delivery device. The needle modules used herein could be used in a medicament delivery device or in a cartridge assembly for attaching to a powerpack of a medicament delivery device. The medicament delivery device could be an autoinjector, for example. An example of a device in which the needle modules described herein could be used is provided in PCT/EP2021/084082, which is hereby incorporated by reference.

Although the ideas described herein primarily focus on needle-based injection, the ideas described herein can be used with medicament delivery members other than needles, such as jet injectors.

From a technical standpoint, it is also feasible to rotate the entire needle module 180 degrees within a medicament delivery device so that the proximal shield is at the distal end, resulting in initially having the needle penetrate the injection site and then subsequently penetrate the cartridge, instead of vice versa.

Typically, the proximal shield, the distal shield and the medicament delivery member hub are coaxial. Various adjustments can be made to the particular shape and features of the components of the needle module, and some example adjustments will now be described. The proximal shield 30 is shown as tubular (and cylindrical), but the shape could be varied, particularly when sterility of the needle module is not required. Similarly, the distal shield 50 is shown as tubular (and cylindrical), but the shape could be varied, particularly when sterility of the needle module is not required.

The proximal shield 30 is shown arranged telescopically inside the distal shield 50. Optionally, the proximal shield 30 and the distal shield 50 are rotationally restricted relative to one another—for example with grooves on one of the proximal shield and the distal shield and ribs on the other of the proximal shield and the distal shield. Similarly, the proximal shield and the needle hub are optionally rotationally restricted relative to one another, for example with grooves on one of the proximal shield and the needle hub and ribs on the other. The proximal shield and the distal shield could be two nested cylinders without rotational restriction, as in some embodiments the contact surfaces such as the second surface 32 and the fourth surface 54 extend the entire way around the axis, meaning that the rotational positions of the components relative to one another are not critical. Similarly, the proximal shield and the needle hub could be two nested cylinders without rotational restriction, as in some embodiments the contact surfaces such as the first surface 31 and the third surface 73 extend the entire way around the axis, meaning that the rotational positions of the components relative to one another are not critical.

The second surface 32 and the fourth surface 54 are shown as both protruding beyond the surface of their respective shields 30, 50, with the second surface 32 protruding away from the axis from the outer surface of the proximal shield 30 and the fourth surface 54 protruding towards the axis from the inner surface of the distal shield 50. Alternatively, only one of the second surface 32 and the fourth surface 54 is on a protrusion. Alternatively, neither of the second surface 32 and the fourth surface 54 is on a protrusion; this could be achieved by providing a material with higher friction on the second surface 32 and/or the fourth surface 54 than on the neighbouring areas of the outer surface/inner surface, for example. Similarly, it is optional to provide the first surface 31 on a protrusion.

Various features of the needle module have fourfold symmetry around the axis; that is, four of each feature (e.g. the first surface 31, the tab 36 of the proximal shield 30 and the protrusion 58 of the distal shield 50) are provided. Instead, one, two or more of each feature could be provided.

The tabs 36 are described as compressible. This is optional, as the same effects can be provided with a non-compressible tab, but compressibility can help vary the friction and can help allow the tabs 36 to pass the protrusions 74 (this could alternatively occur by flexing of the tabs 36 in a non-compressible version, for example by providing the tabs 36 on a flexible arm or by providing optional recesses 38 adjacent to the tabs 36, thereby making flexing of the tabs themselves easier relative to the rest of the proximal shield 30).

The fifth surface 55 and the wall comprising the fifth surface 55 are optional, and the sixth surface 76 could alternatively abut another medicament delivery device component (such as a cartridge or a protrusion of a housing) to limit distal movement of the needle hub 70 relative to the distal shield 50. The recess 59 is also optional, as the cartridge could be aligned using other medicament delivery device components.

The needle hub 70 comprises a base 71 which is shown as cylindrical, though this could be varied depending on the shape of the proximal shield 30, for example. In the depicted example, the protrusions 74 are circumferentially extending ribs, though other shapes could be used. The needle 72 could be a single tube extending through the base, or could comprise a proximal portion and a distal portion, with a hole through the base connecting the proximal portion and the distal portion. The needle could be replaced by a jet injector. The ends of the needle are shown as pointed, though this is also optional.

FIG. 8 shows another needle module comprising a front shield 30 (proximal shield), a needle hub 70 and a rear shield 50 (distal shield).

Concerning the front shield and the needle hub: the inner ribs of the front shield are located inside slots of the needle hub's slots to synchronize axial rotational motion between these two components in a first stroke.

Concerning the front shield and the rear shield: outward protrusions of the front shield slide along the inner surface of the rear shield. They go through the rear shield's outer threads in the first stroke with rotation and then pass straight through the slot in the second stroke.

Concerning the needle hub and the rear shield: the needle hub's thread slides through the inner thread of the rear shield so that when the needle hub is rotated by the front shield in the first stroke, it would also be moved rearward into the cartridge.

Seven particular aspects of the needle module are shown in FIGS. 9 to 11:

1. inner ribs 101 engage slots of the needle hub to synchronise rotational motion between the front shield and the needle hub
2. outward protrusions 102 of the front shield couple with the outer thread of the rear shield so that the front shield can be rotated when it is pushed in the rearward direction
3. slots 103 of the needle hub engage the inner ribs of the front shield so that the needle hub can be rotated with the front shield.

4. the thread 104 of the needle hub is coupled to the inner thread of the rear shield, so that the needle hub can move towards the cartridge when it is rotated by the front shield.
5. the outer thread 105 of the rear shield rotates the front shield when it is pushed in the first stroke.
6. the inner thread 106 of the rear shield leads the needle hub insertion into the cartridge.
7. the straight slot 107 of the rear shield is for the front shield to move straight in the second stroke and insert the needle into the skin.

Figure 12:
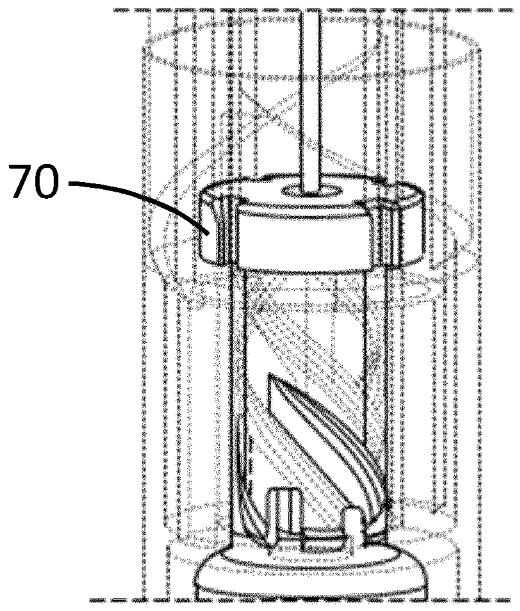
Figure 13:
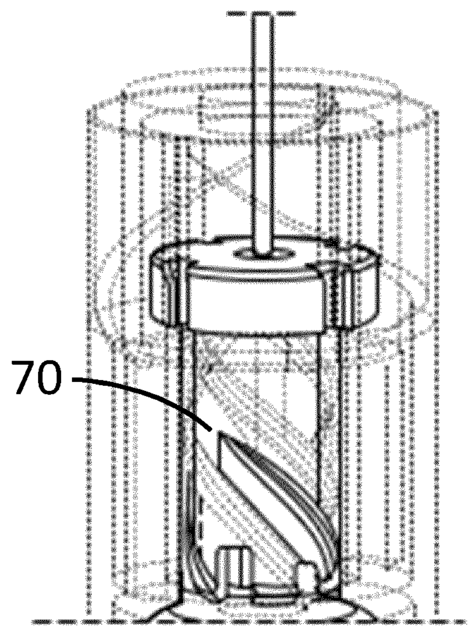

This sequence will now be described with reference to FIGS. 12 and 13. In the first stroke ('$1^{st}$ part stroke'), when the front shield is pushed rearward, it rotates through the outer thread of the rear shield. Its rotational motion also rotates the needle hub and therefore makes it move rearward through the inner thread of the rear shield. In the second stroke ('$2^{nd}$ part stroke'), the front shield is pushed straight through the straight slots of the rear shield. Its inner ribs are still engaged with the needle hub but just slide through it.

In more detail: In the first stroke, when a user presses the needle cover, the front shield would also be pushed rearward and its outward protrusions make the component rotate when they slide through the outer threads of the rear shield. Rotation of the front shield is also transmitted to the needle hub by its inner ribs and makes the needle hub move rearward due to the connection between the inner threads of the rear shield and the thread of the needle hub. Once the distal end of the needle is attached to cartridge and the outward protrusions of the front shield reach the end of the outer thread of the rear shield, it is the end of the first stroke and the beginning of the second stroke. In the second stroke, the outward protrusions of the front shield can slide through the straight slot of the rear shield so there is no rotation involved. Meanwhile, the inner ribs of the front shield also slide through the slots of the needle hub so their coupled features are not effective in this part of the stroke. The second stroke ends when the front shield is entirely pushed into the rear shield and the needle is inserted into the skin at injection site. Then the injection process can begin.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the terms "longitudinal", "longitudinally", "axially" and "axial" refer to a direction extending from the proximal end to the distal end and along the device or components thereof, typically in the direction of the longest extension of the device and/or component.

Similarly, the terms "transverse", "transversal" and "transversally" refer to a direction generally perpendicular to the longitudinal direction.

Generally, all terms used are to be interpreted according to their ordinary meaning in the technical field, unless explicitly defined otherwise herein. All references to a/an/the element, apparatus, member, component, means, etc. are to be interpreted openly as referring to at least one instance of the element, apparatus, member component, means, etc., unless explicitly stated otherwise.

The delivery devices described herein can be used for the treatment and/or prophylaxis of one or more of many different types of disorders. Exemplary disorders include, but are not limited to: rheumatoid arthritis, inflammatory bowel diseases (e.g. Crohn's disease and ulcerative colitis), hypercholesterolaemia, diabetes (e.g. type 2 diabetes), psoriasis, migraines, multiple sclerosis, anaemia, lupus, atopic dermatitis, asthma, nasal polyps, acute hypoglycaemia, obesity, anaphylaxis and allergies. Exemplary types of drugs that could be included in the medicament delivery devices described herein include, but are not limited to, antibodies, proteins, fusion proteins, peptibodies, polypeptides, pegylated proteins, protein fragments, protein analogues, protein variants, protein precursors, and/or protein derivatives. Exemplary drugs that could be included in the delivery devices described herein include, but are not limited to (with non-limiting examples of relevant disorders in brackets): etanercept (rheumatoid arthritis, inflammatory bowel diseases (e.g. Crohn's disease and ulcerative colitis)), evolocumab (hypercholesterolaemia), exenatide (type 2 diabetes), secukinumab (psoriasis), erenumab (migraines), alirocumab (rheumatoid arthritis), methotrexate (amethopterin) (rheumatoid arthritis), tocilizumab (rheumatoid arthritis), interferon beta-1a (multiple sclerosis), sumatriptan (migraines), adalimumab (rheumatoid arthritis), darbepoetin alfa (anaemia), belimumab (lupus), peginterferon beta-1a' (multiple sclerosis), sarilumab (rheumatoid arthritis), semaglutide (type 2 diabetes, obesity), dupilumab (atopic dermatis, asthma, nasal polyps, allergies), glucagon (acute hypoglycaemia), epinephrine (anaphylaxis), insulin (diabetes), atropine and vedolizumab (inflammatory bowel diseases (e.g. Crohn's disease and ulcerative colitis)). Pharmaceutical formulations including, but not limited to, any drug described herein are also contemplated for use in the delivery devices described herein, for example pharmaceutical formulations comprising a drug as listed herein (or a pharmaceutically acceptable salt of the drug) and a pharmaceutically acceptable carrier. Pharmaceutical formulations comprising a drug as listed herein (or a pharmaceutically acceptable salt of the drug) may include one or more other active ingredients, or may be the only active ingredient present.

Various modifications to the embodiments described are possible and will occur to those skilled in the art without departing from the invention which is defined by the following claims.

Certain aspects are summarised by the following clauses.

1. A medicament delivery member module for a medicament delivery device, the medicament delivery member module comprising a proximal shield, a distal shield and a medicament delivery member hub, the medicament delivery member module extending along a longitudinal axis in an axial direction from a proximal end to a distal end,
   wherein the proximal shield comprises a first surface facing towards the longitudinal axis and a second surface facing away from the longitudinal axis, wherein the medicament delivery member hub comprises a third surface facing away from the longitudinal axis and the distal shield comprises a fourth surface facing towards the longitudinal axis,
   wherein the proximal shield is moveable in the axial direction relative to the distal shield from a proximal position to a distal position, wherein the medicament delivery member module is arranged so that in a first part of a movement of the proximal shield from the proximal position to the distal position, the first surface and the third surface are in contact with one another and the second surface and the fourth surface are in contact with one another, and the friction between the first surface and the third surface is greater than the friction between the second surface and the fourth surface, so that during the first part of the movement of the proximal shield from the proximal position to the distal position, the medicament delivery member hub moves with the proximal shield, wherein the medicament delivery member module is arranged so that in a subsequent part (which is after the first part) of the movement of the proximal shield from the proximal position to the distal position, the first surface and the third surface are in contact with one another and the second surface and the fourth surface are spaced apart from one another (typically in the axial direction), and the medicament delivery member hub is restricted from further movement in the distal direction, so that the proximal shield moves in the distal direction relative to both the distal shield and the medicament delivery member hub during the subsequent part of the movement of the proximal shield from the proximal position to the distal position.

2. The medicament delivery member module of clause 1, wherein the first surface and the second surface are both on a protrusion.

3. The medicament delivery member module of clause 2, wherein the protrusion is compressible.

4. The medicament delivery member module of clause 2 or 3, wherein the protrusion is on a tab of the proximal shield.

5. The medicament delivery member module of any of clauses 1 to 4, wherein the tab is at a distal end of the proximal shield.

6. The medicament delivery member module of any of clauses 1 to 5, wherein the third surface comprises a protrusion.

7. The medicament delivery member module of clause 6, wherein the protrusion is a rib that extends circumferentially around the longitudinal axis.

8. The medicament delivery member module of any of clauses 1 to 5, wherein the third surface comprises a plurality of protrusions that are spaced apart from one another in the axial direction.

9. The medicament delivery member module of clause 8, wherein the plurality of protrusions are ribs that extend circumferentially around the longitudinal axis.

10. The medicament delivery member module of any of clauses 1 to 9, wherein the proximal shield is at least partially inside the distal shield.

11. The medicament delivery member module of any of clauses 1 to 10, wherein the medicament delivery member hub is at least partially inside the proximal shield.

12. The medicament delivery member module of any of clauses 1 to 11, wherein the proximal shield, the distal shield and the medicament delivery member hub are coaxial.

13. The medicament delivery member module of any of clauses 1 to 12, wherein the proximal shield is arranged telescopically inside the distal shield.

14. The medicament delivery member module of any of clauses 1 to 13, wherein one or more of the proximal shield and the distal shield comprises a seal that is pierced by the medicament delivery member during movement of the proximal shield relative to the distal shield.

15. The medicament delivery member module of any of clauses 1 to 14, wherein the proximal shield is tubular.

16. The medicament delivery member module of any of clauses 1 to 15, wherein the proximal shield is cylindrical.

17. The medicament delivery member module of any of clauses 1 to 16, wherein the distal shield is tubular.

18. The medicament delivery member module of any of clauses 1 to 17, wherein the distal shield is cylindrical.

19. The medicament delivery member module of any of clauses 1 to 18, wherein the needle hub is cylindrical.

20. The medicament delivery member module of any of clauses 1 to 19, wherein the proximal shield is closer to the proximal end of the needle module than the distal shield.

21. The medicament delivery member module of any of clauses 1 to 20, wherein the needle hub comprises a medicament delivery member.

22. The medicament delivery member module of clause 21, wherein the medicament delivery member is a needle.

23. The medicament delivery member module of any of clauses 1 to 22, wherein the proximal shield is moveable in the axial direction relative to the distal shield from an initial position to the proximal position, wherein in the initial position, the first surface and the third surface are in contact with one another and the second surface and the fourth surface are spaced apart from one another, and wherein the medicament delivery member module is arranged so that the proximal shield and the medicament delivery member hub move in the distal direction relative to the distal shield when the medicament delivery member module moves from the initial position to the proximal position.

24. The medicament delivery member module of any of clauses 1 to 23, wherein the distal shield comprises a fifth surface, wherein the fifth surface faces in the proximal direction, and wherein the medicament delivery member hub comprises a sixth surface, wherein the sixth surface faces in the distal direction, and wherein the fifth surface is arranged to be in contact with the sixth surface during the subsequent part of the movement stroke so that the medicament delivery member hub is restricted from further movement in the distal direction during the subsequent part of the movement stroke.

25. A sub-assembly of a medicament delivery device comprising a cartridge and the medicament delivery member module of any of clauses 1 to 24.

26. The sub-assembly of clause 25 when dependent on any of clauses 1 to 23, wherein the cartridge comprises a fifth surface, wherein the fifth surface faces in the proximal direction, and wherein the medicament delivery member hub comprises a sixth surface, wherein the sixth surface faces in the distal direction, and wherein the fifth surface is arranged to be in contact with the sixth surface during the subsequent part of the movement stroke so that the medicament delivery member hub is restricted from further movement in the distal direction during the subsequent part of the movement stroke.

27. A cartridge assembly for attaching to a powerpack of a medicament delivery device, the cartridge assembly comprising the medicament delivery member module of any of clauses 1 to 24 or the sub-assembly of clause 25 or 26.

28. A medicament delivery device comprising the medicament delivery member module of any of clauses 1 to 24, the sub-assembly of clause 25 or 26, or the cartridge assembly of clause 27.

29. The medicament delivery device of clause 28, wherein the medicament delivery device is an autoinjector.

The invention claimed is:

1. A medicament delivery member module (10) for a medicament delivery device, the medicament delivery member module (10) comprising a proximal shield (30), a distal shield (50) and a medicament delivery member hub (70), the medicament delivery member module (10) extending along a longitudinal axis (12) in an axial direction (13) from a proximal end (14) to a distal end (15), wherein the proximal shield (30) comprises a first surface (31) facing towards the longitudinal axis (12) and a second surface (32) facing away from the longitudinal axis (12), wherein the medicament delivery member hub (70) comprises a third surface (73) facing away from the longitudinal axis (12) and the distal shield (50) comprises a fourth surface (54) facing towards the longitudinal axis, wherein the proximal shield (30) is moveable in the axial direction (13) relative to the distal shield (50) from a proximal position to a distal position, wherein the medicament delivery member module (10) is arranged so that in a first part of a movement of the proximal shield (30) from the proximal position to the distal position, the first surface (31) and the third surface (73) are in contact with one another and the second surface (32) and the fourth surface (54) are in contact with one another, and the friction between the first surface (31) and the third surface (73) is greater than the friction between the second surface (32) and the fourth surface (54), so that during the first part of the movement of the proximal shield (30) from the proximal position to the distal position, the medicament delivery member hub (70) moves with the proximal shield (30), wherein the medicament delivery member module (10) is arranged so that in a subsequent part of the movement of the proximal shield (30) from the proximal position to the distal position, the first surface (31) and the third surface (73) are in contact with one another and the second surface (32) and the fourth surface (54) are spaced apart from one another, and the medicament delivery member hub (70) is restricted from further movement in the distal direction, so that the proximal shield (30) moves in the distal direction relative to both the distal shield (50) and the medicament delivery member hub (70) during the subsequent part of the movement of the proximal shield (30) from the proximal position to the distal position.

2. The medicament delivery member module (10) of claim 1, wherein the first surface and the second surface are both on a protrusion (36).

3. The medicament delivery member module of claim 2, wherein the protrusion (36) is compressible.

4. The medicament delivery member module (10) of claim 2, wherein the protrusion (36) is on a tab of the proximal shield (30).

5. The medicament delivery member module (10) of claim 1, wherein the third surface (73) comprises a protrusion (74).

6. The medicament delivery member module of claim 5, wherein the protrusion (74) is a rib that extends circumferentially around the longitudinal axis (12).

7. The medicament delivery member module (10) of claim 1, wherein the third surface comprises a plurality of protrusions (74) that are spaced apart from one another in the axial direction.

8. The medicament delivery member module (10) of claim 7, wherein the plurality of protrusions (74) are ribs that extend circumferentially around the longitudinal axis (12).

9. The medicament delivery member module (10) of claim 1, wherein the proximal shield (30) is arranged telescopically inside the distal shield (50).

10. The medicament delivery member module (10) of claim 1, wherein the proximal shield (30) is moveable in the axial direction (13) relative to the distal shield (50) from an initial position to the proximal position, wherein in the initial position, the first surface (31) and the third surface (73) are in contact with one another and the second surface (32) and the fourth surface (54) are spaced apart from one another, and wherein the medicament delivery member module (10) is arranged so that the proximal shield (30) and the medicament delivery member hub (70) move in the distal direction relative to the distal shield (50) when the medicament delivery member module (10) moves from the initial position to the proximal position.

11. The medicament delivery member module (10) of claim 1, wherein the distal shield (50) comprises a fifth surface (55), wherein the fifth surface (55) faces in the proximal direction, and wherein the medicament delivery member hub (70) comprises a sixth surface (76), wherein the sixth surface (76) faces in the distal direction, and wherein the fifth surface (55) is arranged to be in contact with the sixth surface (76) during the subsequent part of the movement stroke so that the medicament delivery member hub (70) is restricted from further movement in the distal direction during the subsequent part of the movement stroke.

12. A sub-assembly of a medicament delivery device comprising a cartridge and the medicament delivery member module (10) of claim 1.

13. The sub-assembly of claim 12, wherein the cartridge comprises a fifth surface, wherein the fifth surface faces in the proximal direction, and wherein the medicament delivery member hub (70) comprises a sixth surface (76), wherein the sixth surface (76) faces in the distal direction, and wherein the fifth surface is arranged to be in contact with the sixth surface (76) during the subsequent part of the movement stroke so that the medicament delivery member hub (70) is restricted from further movement in the distal direction during the subsequent part of the movement stroke.

14. A cartridge assembly for attaching to a powerpack of a medicament delivery device, the cartridge assembly comprising the medicament delivery member module (10) of claim 1.

15. A medicament delivery device comprising the medicament delivery member module (10) of claim 1.

* * * * *